US008450535B2

(12) United States Patent
Johnston et al.

(10) Patent No.: US 8,450,535 B2
(45) Date of Patent: *May 28, 2013

(54) ETHANOL PRODUCTION FROM ACETIC ACID UTILIZING A COBALT CATALYST

(75) Inventors: Victor J. Johnston, Houston, TX (US); Barbara F. Kimmich, Bernardsville, NJ (US); Jan Cornelis van der Waal, Delft (NL); James H. Zink, League City, TX (US); Virginie Zuzaniuk, Haarlem, NH (US); Josefina T. Chapman, Houston, TX (US); Laiyuan Chen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/079,679

(22) Filed: Apr. 4, 2011

(65) Prior Publication Data

US 2011/0282109 A1    Nov. 17, 2011

Related U.S. Application Data

(63) Continuation-in-part of application No. 13/056,470, filed as application No. PCT/US2009/004197 on Jul. 20, 2009.

(51) Int. Cl.
*C07C 29/149* (2006.01)

(52) U.S. Cl.
USPC .......................................... 568/885; 568/861

(58) Field of Classification Search
USPC ................................................. 568/885, 861
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,136,704 A | 11/1938 | Mitchell |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Adam |
| 3,702,886 A | 11/1972 | Araguer |
| 3,729,429 A | 4/1973 | Robson |
| 3,990,952 A | 11/1976 | Katzen |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz |
| 4,317,918 A | 3/1982 | Takano |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes |
| 4,398,039 A | 8/1983 | Pesa |
| 4,399,305 A | 8/1983 | Schreck |
| 4,421,939 A | 12/1983 | Kiff |
| 4,443,639 A | 4/1984 | Pesa |
| 4,465,854 A | 8/1984 | Pond |
| 4,471,136 A | 9/1984 | Larkins |
| 4,480,115 A | 10/1984 | McGinnis |
| 4,517,391 A | 5/1985 | Schuster |
| 4,521,630 A | 6/1985 | Wattimena |
| 4,550,185 A | 10/1985 | Mabry |
| 4,581,473 A | 4/1986 | Polichnowski |
| 4,613,700 A | 9/1986 | Maki |
| 4,620,050 A | 10/1986 | Cognion |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,826,795 A | 5/1989 | Kitson |
| 4,843,170 A | 6/1989 | Isshiki |
| 4,886,905 A | 12/1989 | Larkins, Jr. |
| 4,902,823 A | 2/1990 | Wunder |
| 4,978,778 A | 12/1990 | Isshiki |
| 4,985,572 A | 1/1991 | Kitson |
| 4,990,655 A | 2/1991 | Kitson |
| 5,008,235 A | 4/1991 | Wegman |
| 5,061,671 A | 10/1991 | Kitson |
| 5,124,004 A | 6/1992 | Grethlein |
| 5,137,861 A | 8/1992 | Shih |
| 5,149,680 A | 9/1992 | Kitson |
| 5,155,084 A | 10/1992 | Horn |
| 5,185,308 A | 2/1993 | Bartley |
| 5,241,106 A | 8/1993 | Inoue |
| 5,243,095 A | 9/1993 | Roberts |

(Continued)

FOREIGN PATENT DOCUMENTS

| | | |
|---|---|---|
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0285420 | 10/1988 |
| EP | 0285420 B1 | 10/1988 |
| EP | 0330853 | 8/1989 |
| EP | 0372847 | 6/1990 |
| EP | 0372847 A2 | 6/1990 |

(Continued)

OTHER PUBLICATIONS

Non-final Office Action for U.S. Appl. No. 13/215,829 mailed Sep. 11, 2012.
Non-final Office Action for U.S. Appl. No. 13/056,470 mailed Aug. 31, 2012.
Alcala, et al., (2005). Experimental and DFT studies of the conversion of ethanol and acetic acid on PtSn-based catalysts, Journal of Physical Chemistry, 109(6), 2074-2085.

(Continued)

*Primary Examiner* — Elvis O Price

(57) ABSTRACT

A process for the selective and direct formation of ethanol from acetic acid comprising contacting a feed stream containing acetic acid and hydrogen in vapor form at an elevated temperature with a hydrogenation catalyst comprising cobalt and one or more metals selected from the group consisting of palladium, platinum, rhodium, ruthenium, rhenium, iridium, chromium, copper, tin, molybdenum, tungsten, vanadium, zinc and iron on a catalyst support.

20 Claims, No Drawings

U.S. PATENT DOCUMENTS

| | | | |
|---|---|---|---|
| 5,306,845 | A | 4/1994 | Yokohama |
| 5,350,504 | A | 9/1994 | Dessau |
| 5,426,246 | A | 6/1995 | Nagahara |
| 5,475,144 | A | 12/1995 | Watson |
| 5,476,827 | A | 12/1995 | Ferrero |
| RE35,377 | E | 11/1996 | Steinberg |
| 5,585,523 | A | 12/1996 | Weiguny |
| 5,691,267 | A | 11/1997 | Nicolau |
| 5,719,315 | A | 2/1998 | Tustin |
| 5,731,456 | A | 3/1998 | Tustin |
| 5,767,307 | A | 6/1998 | Ramprasad |
| 5,821,111 | A | 10/1998 | Grady |
| 5,849,657 | A | 12/1998 | Rotgerink |
| 5,861,530 | A | 1/1999 | Atkins |
| 5,945,570 | A | 8/1999 | Arhancet |
| 5,955,397 | A | 9/1999 | Didillon |
| 5,973,193 | A | 10/1999 | Crane |
| 6,040,474 | A | 3/2000 | Jobson |
| 6,049,008 | A | 4/2000 | Roberts |
| 6,093,845 | A | 7/2000 | van Acker |
| 6,114,571 | A | 9/2000 | Abel |
| 6,121,498 | A | 9/2000 | Tustin |
| 6,232,352 | B1 | 5/2001 | Vidalin |
| 6,232,504 | B1 | 5/2001 | Barteau |
| 6,294,703 | B1 | 9/2001 | Hara |
| 6,462,231 | B1 | 10/2002 | Yanagawa |
| 6,472,555 | B2 | 10/2002 | Choudary |
| 6,486,366 | B1 | 11/2002 | Ostgard |
| 6,495,730 | B1 | 12/2002 | Konishi |
| 6,509,180 | B1 | 1/2003 | Verser |
| 6,509,290 | B1 | 1/2003 | Vaughn |
| 6,559,333 | B1 | 5/2003 | Brunelle |
| 6,603,038 | B1 | 8/2003 | Hagemeyer |
| 6,632,330 | B1 | 10/2003 | Colley |
| 6,657,078 | B2 | 12/2003 | Scates |
| 6,685,754 | B2 | 2/2004 | Kindig |
| 6,693,213 | B1 | 2/2004 | Kolena |
| 6,696,596 | B1 | 2/2004 | Herzog |
| 6,727,380 | B2 | 4/2004 | Ellis |
| 6,765,110 | B2 | 7/2004 | Warner |
| 6,768,021 | B2 | 7/2004 | Horan |
| 6,812,372 | B2 | 11/2004 | Janssen |
| 6,852,877 | B1 | 2/2005 | Zeyss |
| 6,903,045 | B2 | 6/2005 | Zoeller |
| 6,906,228 | B2 | 6/2005 | Fischer |
| 6,927,048 | B2 | 8/2005 | Verser |
| 7,074,603 | B2 | 7/2006 | Verser |
| 7,084,312 | B1 | 8/2006 | Huber |
| 7,297,236 | B1 | 11/2007 | Vander Griend |
| 7,351,559 | B2 | 4/2008 | Verser |
| 7,375,049 | B2 | 5/2008 | Hayes |
| 7,425,657 | B1 | 9/2008 | Elliott |
| 7,507,562 | B2 | 3/2009 | Verser |
| 7,518,014 | B2 | 4/2009 | Kimmich |
| 7,538,060 | B2 | 5/2009 | Barnicki |
| 7,553,397 | B1 | 6/2009 | Colley |
| 7,572,353 | B1 | 8/2009 | Vander Griend |
| 7,608,744 | B1 | 10/2009 | Johnston |
| 7,863,489 | B2 | 1/2011 | Johnston |
| 7,884,253 | B2 | 2/2011 | Stites |
| 2003/0013908 | A1 | 1/2003 | Horan |
| 2003/0077771 | A1 | 4/2003 | Verser |
| 2003/0104587 | A1 | 6/2003 | Verser |
| 2003/0114719 | A1 | 6/2003 | Fischer |
| 2003/0191020 | A1 | 10/2003 | Bharadwaj |
| 2004/0195084 | A1 | 10/2004 | Hetherington |
| 2006/0019360 | A1 | 1/2006 | Verser |
| 2006/0102520 | A1 | 5/2006 | Lapinski |
| 2006/0106246 | A1 | 5/2006 | Warner |
| 2006/0127999 | A1 | 6/2006 | Verser et al. |
| 2007/0270511 | A1 | 11/2007 | Melnichuk |
| 2008/0207953 | A1 | 8/2008 | Houssin |
| 2009/0005588 | A1 | 1/2009 | Hassan |
| 2009/0023192 | A1 | 1/2009 | Verser |
| 2009/0081749 | A1 | 3/2009 | Verser |
| 2009/0166172 | A1 | 7/2009 | Casey |
| 2009/0221725 | A1 | 9/2009 | Chornet |
| 2009/0318573 | A1 | 12/2009 | Stites |
| 2009/0326080 | A1 | 12/2009 | Chornet |
| 2010/0016454 | A1 | 1/2010 | Gracey |
| 2010/0029980 | A1 | 2/2010 | Johnston |
| 2010/0029995 | A1 | 2/2010 | Johnston |
| 2010/0029996 | A1 | 2/2010 | Danjo et al. |
| 2010/0030001 | A1 | 2/2010 | Chen |
| 2010/0030002 | A1 | 2/2010 | Johnston |
| 2010/0113843 | A1 | 5/2010 | Lee |
| 2010/0121114 | A1 | 5/2010 | Weiner |
| 2010/0168493 | A1 | 7/2010 | LePeltier |
| 2010/0196789 | A1 | 8/2010 | Fisher |
| 2010/0197485 | A1 | 8/2010 | Johnston |
| 2010/0249479 | A1 | 9/2010 | Berg-Slot |

FOREIGN PATENT DOCUMENTS

| | | |
|---|---|---|
| EP | 0400904 | 12/1990 |
| EP | 0408528 | 1/1991 |
| EP | 0198682 | 3/1991 |
| EP | 0285786 | 5/1993 |
| EP | 0990638 | 4/2000 |
| EP | 0990638 A1 | 4/2000 |
| EP | 1262234 | 12/2002 |
| EP | 1262234 A2 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 4193304 | 7/1992 |
| JP | 6116182 | 4/1994 |
| JP | 10306047 | 11/1998 |
| JP | 11147845 | 6/1999 |
| JP | 2001046874 | 2/2001 |
| JP | 2001157841 | 6/2001 |
| WO | 8303409 | 10/1983 |
| WO | 03040037 | 5/2003 |
| WO | 2005102513 | 11/2005 |
| WO | 2009009322 | 1/2009 |
| WO | 2009009323 | 1/2009 |
| WO | 2009063176 | 5/2009 |
| WO | 2009086839 | 7/2009 |
| WO | 2009105860 | 9/2009 |
| WO | 2010014145 | 2/2010 |
| WO | 2010014153 | 2/2010 |
| WO | 2010055285 | 5/2010 |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Brunauer Emmett and Teller, J. Am. Chem. Soc. 60, 309 (1938).

English langauage abstract for JP 4-193304 A.

English langauge abstract for EP 0 192 587 A1.

English langauge abstract for EP 0 330 853 A2.

English langauge abstract for JP 2001-157841 A.

English language abstract for EP 0 137 749 A2.

English language abstract for JP 10-306047 A.

English language abstract for JP 11-147845 A.

English language abstract for JP 2001-046874 A.

English language abstract for JP 6-116182 A.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

International Preliminary Report on Patentability for PCT/US2009/004197 dated Aug. 10, 2010.

International Search Report and Written Opinion for PCT/US2009/004195 mailed Mar. 26, 2010.

International Search Report and Written Opinion for PCT/US2009/004197 mailed Mar. 24, 2010.

Ordonez et al., The role of metal and support sites on the hydrogenation of acetic acid on Ru-based catalysts, 21ST NAM San Francisco, CA, Jun. 10, 2009.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Pestman et al., (1997). Reactions of Carboxylic Acids on Oxides, Journal of Catalysis 168, 255-264.

Pestman et al., (1998). Identification of the Active Sites in the Selective Hydrogenation of Acetic Acid to Acetaldehyde on Iron Oxide Catalysts, Journal of Catalysis, 174, 142-152.

Pestman et al., The formation of ketones and aldehydes from carboxylic acids, structure-activity relationship for two competitive reactions, Journal of Molecular Catalysis A: Chemical 103 Jun. 14, 1995, 175-180.

Proc. Roy Soc. A314, pp. 473-498 (1970).

Rachmady, Acetic Acid Reduction by H2 on Bimetallic Pt Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-dervied syngas," Chemical Society Review, 2007, vol. 36, pp. 1514-1528.

Subramani et al., "A Review of Recent Literature to Search for an Efficient Catalytic Process for the Conversion of Syngas to Ethanol," Energy & Fuels, 2008, vol. 22, pp. 814-839.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ETHANOL PRODUCTION FROM ACETIC ACID UTILIZING A COBALT CATALYST

CROSS REFERENCE TO RELATED APPLICATIONS

This application is a continuation-in-part application of U.S. patent application Ser. No. 13/056,470 filed on Jan. 28, 2011, which is a national stage application of PCT/US2009/004197, filed on Jul. 20, 2009, which claims priority to U.S. patent application Ser. No. 12/221,239, filed Jul. 31, 2008, and which issued as U.S. Pat. No. 7,608,744, the priority of which is hereby claimed and the disclosures of which are incorporated in their entirety herein by reference.

FIELD OF THE INVENTION

The present invention relates generally to a process for the production of ethanol from acetic acid. More specifically, the present invention relates to a process including hydrogenating acetic acid utilizing a catalyst composed of cobalt and one or more metals on a support to form ethanol with high selectivity.

BACKGROUND OF THE INVENTION

There is a long felt need for an economically viable process to convert acetic acid to ethanol. Ethanol is an important commodity feedstock for a variety of industrial products and is also used as a fuel additive with gasoline. Ethanol can readily be dehydrated to ethylene, which can then be converted to a variety of products, both polymeric and small molecule-based. Ethanol is conventionally produced from feedstocks where price fluctuations are becoming more significant. That is, fluctuating natural gas and crude oil prices contribute to fluctuations in the cost of conventionally produced, petroleum, natural gas or corn or other agricultural product-sourced ethanol, making the need for alternative sources of ethanol all the greater when oil prices and/or agricultural product prices rise.

It has been reported that ethanol can be produced from the hydrogenation of acetic acid, but most of these processes feature several drawbacks for a commercial operation. For instance, U.S. Pat. No. 2,607,807 discloses that ethanol can be formed from acetic acid over a ruthenium catalyst at extremely high pressures of 700-950 bars in order to achieve yields of around 88%, whereas low yields of only about 40% are obtained at pressures of about 200 bar. Nevertheless, both of these conditions are unacceptable and uneconomical for a commercial operation.

More recently, it has been reported that ethanol can be produced from hydrogenating acetic acid using a cobalt catalyst again at superatmospheric pressures such as about 40 to 120 bar. See, for example, U.S. Pat. No. 4,517,391 to Shuster et al. However, the only example disclosed therein employs reaction pressure in the range of about 300 bar still making this process undesirable for a commercial operation. In addition, the process calls for a catalyst containing no less than 50 percent cobalt by weight plus one or more members selected from the group consisting of copper, manganese, molybdenum, chromium, and phosphoric acid, thus rendering the process economically non-viable. Although there is a disclosure of use of simple inert catalyst carriers to support the catalyst materials, there is no specific example of supported metal catalysts.

U.S. Pat. No. 5,149,680 to Kitson et al. describes a process for the catalytic hydrogenation of carboxylic acids and their anhydrides to alcohols and/or esters utilizing a platinum group metal alloy catalysts. The catalyst is comprised of an alloy of at least one noble metal of group VIII of the Periodic Table and at least one metal capable of alloying with the group VIII noble metal, admixed with a component comprising at least one of the metals rhenium, tungsten or molybdenum. Although it has been claimed therein that improved selectivity to alcohols are achieved over the prior art references it was still reported that 3 to 9 percent of alkanes, such as methane and ethane are formed as by-products during the hydrogenation of acetic acid to ethanol under their optimal catalyst conditions.

U.S. Pat. No. 4,777,303 to Kitson et al. describes a process for the productions of alcohols by the hydrogenation of carboxylic acids. The catalyst used in this case is a heterogeneous catalyst comprising a first component which is either molybdenum or tungsten and a second component which is a noble metal of Group VIII of the Periodic Table of the elements, optionally on a support, for example, a high surface area graphitized carbon. The selectivity to a combined mixture of alcohol and ester is reported to be only in the range of about 73 to 87 percent with low conversion of carboxylic acids at about 16 to 58 percent. In addition, no specific example of conversion of acetic acid to ethanol is provided.

U.S. Pat. No. 4,804,791 to Kitson et al. describes another process for the productions of alcohols by the hydrogenation of carboxylic acids. In this process, ethanol is produced from acetic acid or propanol is produced from propionic acid by contacting either acetic acid or propionic acid in the vapor phase with hydrogen at elevated temperature and a pressure in the range from 1 to 150 bar in the presence of a catalyst comprising as essential components (i) a noble metal of Group VIII of the Periodic Table of the elements, and (ii) rhenium, optionally on a support, for example a high surface area graphitized carbon. The conversion of acetic acid to ethanol ranged from 0.6% to 69% with selectivity to ethanol was in the range of about 6% to 97%.

From the foregoing it is apparent that the need remains for processes and catalysts having a desirable selectivity to ethanol and employing active phases that are readily available and generally inexpensive.

SUMMARY OF THE INVENTION

In a first embodiment, the present invention is directed to a process for selective and direct formation of ethanol from acetic acid comprising contacting a feed stream comprising acetic acid and hydrogen in vapor form at a temperature of 125° C. to 300° C. with a hydrogenation catalyst comprising cobalt and one or more metals selected from the group consisting of palladium, platinum, rhodium, ruthenium, rhenium, iridium, chromium, copper, tin, molybdenum, tungsten, vanadium, zinc, and iron on a catalyst support.

In a second embodiment, the present invention is directed to a process for selective and direct formation of ethanol from acetic acid comprising contacting a feed stream comprising acetic acid and hydrogen in vapor form at a temperature of 125° C. to 300° C. with a hydrogenation catalyst comprising from 0.1 wt. % to 20 wt. % cobalt and from 0.1 wt. % to 20 wt. % iron on a catalyst support.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Mole percent (mole % or %) and like terms refer to mole percent unless otherwise indicated. Weight percent (wt % or %) and like terms refer to weight percent unless otherwise indicated.

"Conversion" is expressed as a mole percentage based on acetic acid in the feed. The conversion of acetic acid (AcOH) is calculated from gas chromatography (GC) data using the following equation:

$$\text{AcOH conversion (\%)} = 100 * \frac{\text{mmol AcOH in (feed stream)} - \text{mmol AcOH out } (GC)}{\text{mmol AcOH in (feed stream)}}$$

"Selectivity" is expressed as a mole percent based on converted acetic acid. For example, if the conversion is 50 mole % and 50 mole % of the converted acetic acid is converted to ethanol, we refer to the ethanol selectivity as 50%. Selectivity to ethanol (EtOH) is calculated from gas chromatography (GC) data using the following equation:

$$\text{Selectivity to EtOH (\%)} = 100 * \frac{\text{mmol EtOH out } (GC)}{\frac{\text{Total mmol C out } (GC)}{2} - \text{mmol AcOH out } (GC)}$$

Weight percent of a catalyst metal is based on metal weight and the total dry weight of metal and support.

The reaction proceeds in accordance with the following chemical equation:

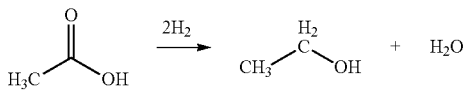

In accordance with the invention, conversion of acetic acid to ethanol can be carried out in a variety of configurations, such as for example in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce ethanol. Any suitable particle size may be used depending upon the type of reactor, throughput requirements and so forth.

The catalyst of the present invention comprises cobalt and one or more metals selected from the group consisting of palladium, platinum, rhodium, ruthenium, rhenium, iridium, chromium, copper, tin, molybdenum, tungsten, vanadium, zinc, iron and a mixture thereof. In some embodiments, cobalt is present in the catalyst preferably from 0.1 wt. % to 20 wt. %, e.g., from 0.1 to 15 wt. %, from 0.1 wt. % to 10 wt. %, from 0.5 to 5.0 wt. % or from 5.0 to 20 wt. %, and the one or metals is present in the catalyst preferably in an amount from 0.1 and 20 wt. %, e.g., from 0.1 to 10 wt. %, from 0.1 to 5 wt. % or 0.1 to 2.5 wt. %. For purposes of the present specification, unless otherwise indicated, weight percent is based on the total weight of the catalyst including metal and support. The metals in the catalyst may be present in elemental form or in the form of one or more metal oxides. For purposes of determining the weight percent of the metals in the catalyst, the weight of any oxygen that is bound to the metal is ignored, although the weight of the oxygen is factored in the total weight of the catalyst. For convenience, the present specification refers to the molybdenum carbide as the primary catalyst and any additional metals as promoter metals. This should not be taken as an indication of the underlying mechanism of the catalytic activity. The metals may be alloyed with one another or may comprise a non-alloyed metal solution or mixture.

In some embodiments, a catalyst of the present invention comprises cobalt and one or more metals in a mole ratio of the cobalt to the one or more metals from 10:1 to 1:10, e.g., from 4:1 to 1:4, or from 2:1 to 1:2.

As noted earlier, it is further preferred that the catalysts that are suitable in the process of this invention contain optionally a second and/or a third metal supported on the same catalyst support. The following metals may be mentioned as those metals suitable as a second and/or third metals without any limitation: palladium, platinum, rhodium, ruthenium, rhenium, iridium, chromium, copper, tin, molybdenum, tungsten, vanadium, zinc, iron and a mixture thereof. Typically, it is preferred that cobalt in combination with at least one other metal on a suitable support can be used as a hydrogenating catalyst. In a preferred embodiment, the catalyst comprising cobalt and iron. For example, the catalyst may comprise from 5 to 20 wt. % cobalt and 0.1 to 10 wt. % iron. Thus cobalt in combination with either palladium or platinum are particularly preferred. Similarly, cobalt in combination with ruthenium, chromium or vanadium is also preferred. Examples of metals that can be used with cobalt as a third metal include without any limitation any of the other metals listed above, such as for example rhodium, iridium, copper, tin, molybdenum, iron, and zinc.

Various catalyst supports known in the art can be used to support the catalysts of this invention. Examples of such supports include without any limitation, zeolite, iron oxide, silica, alumina, titania, zirconia, silica-alumina, magnesium oxide, calcium silicate, carbon, graphite and mixtures thereof. Preferred supports are silica, alumina, calcium silicate, carbon, zirconia and titania. More preferably silica is used as a catalyst support in the process of this invention. It is also important to note that higher the purity of silica better it is preferred as a support in this invention. Another preferred catalyst support is calcium silicate.

As will be appreciated by those of ordinary skill in the art, the support materials should be selected such that the catalyst system is suitably active, selective and robust under the process conditions employed for the formation of ethanol. Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica and mixtures thereof. Other supports may be used in some embodiments of the present invention, including without limitation, alumina, metasilicate, carbon, zirconia, titania, magnesium oxide, iron oxide, yttria, and zeolite, and mixtures thereof.

In one embodiment of this invention the preferred catalyst support is carbon. Various forms of carbon known in the art that are suitable as catalyst support can be used in the process of this invention. Particularly preferred carbon support is a graphitized carbon, particularly the high surface area graphitized carbon as described in Great Britain Patent No. 2,136,704. The carbon is preferably in particulate form, for example, as pellets. The size of the carbon particles will depend on the pressure drop acceptable in any given reactor (which gives a minimum pellet size) and reactant diffusion constraint within the pellet (which gives a maximum pellet size).

The carbon catalyst supports that are suitable in the process of this invention preferably porous carbon catalyst supports. With the preferred particle sizes the carbon will need to be porous to meet the preferred surface area characteristics.

The catalyst supports including the carbon catalyst supports may be characterized by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473-498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred carbon catalyst supports for use in the present invention have a BET surface area of at least 100 m$^2$/g, more preferably at least 200 m$^2$/g, most preferably at least 300 m$^2$/g. The BET surface area is preferably not greater than 1000 m$^2$/g, more preferably not greater than 750 m$^2$/g.

The preferred carbon support may be prepared by heat treating a carbon-containing starting material. The starting material may be an oleophillic graphite e.g. prepared as disclosed in Great Britain Patent No. 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than these indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° C. and 600° C. when oxygen (e.g. as air) is used as the oxidizing agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidizing agents are steam, carbon dioxide, and gases containing molecular oxygen e.g. air. The oxidation is preferably carried out to give a carbon weight loss of at least 10 weight percent based on weight of carbon subjected to the oxidation step, more preferably at least 15 weight percent.

The weight loss is preferably not greater than 40 weight percent of the carbon subjected to the oxidation step, more preferably not greater than 25 weight percent of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

In some embodiments, the support comprises a support modifier, such as an acidic or basic modifier, having a low volatility or that is non-volatile. Low volatility modifiers have a rate of loss that is low enough such that the acidity of the support modifier is not reversed during the life of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Exemplary acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, $Bi_2O_3$.

Suitable basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the support modifier is selected from the group consisting of oxides and metasilicates of any of sodium, potassium, magnesium, calcium, scandium, yttrium, and zinc, and mixtures of any of the foregoing. Preferably, the support modifier is a calcium silicate, more preferably calcium metasilicate ($CaSiO_3$). If the support modifier comprises calcium metasilicate, it is preferred that at least a portion of the calcium metasilicate is in crystalline form.

The total weight of the modified support, which includes the support material and the support modifier, based on the total weight of the catalyst, preferably is from 75 wt. % to 99.9 wt. %, e.g., from 78 wt. % to 97 wt. %, or from 80 wt. % to 95 wt. %. The support modifier preferably is provided in an amount sufficient to adjust the acidity of the overall catalyst. For example, for basic modifiers the amount of support modifier preferably is sufficient to reduce the number or reduce the availability of active Brønsted acid sites, and more preferably to ensure that the surface of the support is substantially free of active Brønsted acid sites. In some embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In some embodiments, the support material may be present in an amount from 25 wt. % to 99 wt. %, e.g., from 30 wt. % to 97 wt. % or from 35 wt. % to 95 wt. %.

In one embodiment, the support material is a silicaceous support material selected from the group consisting of silica, silica/alumina, a Group IIA silicate such as calcium metasilicate, pyrogenic silica, high purity silica and mixtures thereof. In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. When calcium metasilicate is used as a support modifier, it is not necessary to be quite as strict about the purity of the silica used as the support material although aluminum remains undesirable and will not normally be added intentionally. The aluminum content of such silica, for example, may be less than 10 wt. %, e.g., less than 5 wt. % or less than 3 wt. %. In cases where the support comprises a support modifier in the range of from 2 wt. % to 10 wt. %, larger amount of acidic impurities, such as aluminum, can be tolerated so long as they are substantially counter-balanced by an appropriate amount of a support modifier.

The surface area of the silicaceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the silicaceous support material, e.g., silica, preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 $g/cm^3$, e.g., from 0.2 to 0.9 $g/cm^3$ or from 0.5 to 0.8 $g/cm^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485, the entireties of which are incorporated herein by reference.

As already noted above, other metals that can preferably be used as second metal with cobalt include ruthenium, iron, chromium and vanadium. In each of these cases cobalt loading of 4 to 12 weight percent with second metal, i.e., ruthenium, chromium or vanadium loading of about 0.5 to 2 weight percent are preferred. If a third metal is employed, its loading can also be in the range of about 0.5 weight percent to about 2 weight percent, however, higher levels of metal loadings can also be used depending upon the type of metal and the catalyst support used.

The metal impregnation can be carried out using any of the known methods in the art. Typically, before impregnation the supports are dried at 120° C. and shaped to particles having size distribution in the range of about 0.2 to 0.4 mm Optionally the supports may be pressed, crushed and sieved to a desired size distribution. Any of the known methods to shape the support materials into desired size distribution can be employed.

For supports having low surface area, such as for example alpha-alumina, the metal solutions are added in excess until complete wetness or excess liquid impregnation so as to obtain desirable metal loadings.

As noted above, the hydrogenation catalysts used in the process of this invention are at least bimetallic having cobalt as the main metal. Generally, without intending to be bound by any theory, it is believed that one metal acts as a promoter metal and the other metal is the main metal. For instance, in the instant process of the invention, cobalt is considered to be main metal for preparing hydrogenation catalysts of this invention. The main metal can be combined with a promoter metal such as tungsten, vanadium, molybdenum, chromium, zinc or iron. However, it should be noted that sometimes main metal can also act as a promoter metal or vice versa. For example, nickel can be used as a promoter metal when iron is used as a main metal. Similarly, chromium can be used as a main metal in conjunction with copper (i.e., Cu—Cr as main bimetallic metals), which can further be combined with promoter metals such as cerium, magnesium or zinc.

The bimetallic catalysts are generally impregnated in two steps. First, the "promoter" metal is added, followed by "main" metal. Each impregnation step is followed by drying and calcination. The bimetallic catalysts may also be prepared by co-impregnation. In the case of trimetallic Cu/Crcontaining catalysts as described above, a sequential impregnation may be used, starting with the addition of the "promoter" metal. The second impregnation step may involve co-impregnation of the two principal metals, i.e., Cu and Cr. For example, Cu—Cr—Co on $SiO_2$ may be prepared by a first impregnation of chromium nitrate, followed by the co-impregnation of copper and cobalt nitrates. Again, each impregnation is followed by drying and calcinations. In most cases, the impregnation may be carried out using metal nitrate solutions. However, various other soluble salts which upon calcination releases metal ions can also be used. Examples of other suitable metal salts for impregnation include metal hydroxide, metal oxide, metal acetate, ammonium metal oxide, such as ammonium heptamolybdate hexahydrate, metal acids, such as perrhenic acid solution, metal oxalate, and the like.

Thus in one embodiment of this invention, there is provided a hydrogenation catalyst wherein the catalyst support is graphite with a bimetallic loading of cobalt and palladium. In this aspect of the invention, the loading of cobalt is about ten (10) weight percent and the loading of palladium is about one (1) weight percent. A loading level of cobalt at five (5) weight percent and loading level of palladium at 0.5 weight percent can also be employed if so desired.

In another embodiment of this invention, there is further provided a hydrogenation catalyst wherein the catalyst support is high purity silica with a bimetallic loading of cobalt and platinum. In this aspect of the invention, the loading of cobalt is about ten (10) weight percent and the loading of platinum is about one (1) weight percent. Again in this aspect of the invention, loading levels of cobalt at five (5) weight percent and loading levels of platinum at 0.5 weight percent can also be employed.

In another embodiment of this invention, there is further provided a hydrogenation catalyst wherein the catalyst support is silica with a bimetallic loading of cobalt and iron. In this aspect of the invention, the loading of cobalt is from 5 wt. % to 20 wt. % and the loading of iron is from 0.1 wt. % to 5 wt. %.

In general, by the practice of this invention acetic acid can selectivity be converted to ethanol at very high rates. Preferably, the catalyst selectivity to ethoxylates is at least 40%, e.g., at least 50%, or at least 60%. As used herein, the term "ethoxylates" refers specifically to the compounds ethanol, acetaldehyde, and ethyl acetate. The selectivity to ethanol in general is very high and may be at least 40 percent. Under preferred reaction conditions, acetic acid is selectively converted to ethanol at a selectivity of about 60 percent or more preferably at a selectivity of at least 80 percent. Most preferably ethanol selectivity is at least 95 percent. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour, or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 grams of ethanol per kilogram catalyst per hour or from 600 to 2,000 grams of ethanol per kilogram catalyst per hour.

In another aspect of the process of this invention, the hydrogenation is carried out at a pressure just sufficient to overcome the pressure drop across the catalytic bed. In some embodiments, the hydrogenation of acetic acid to form ethanol may be carried out in the vapor or liquid form under a wide variety of conditions. Preferably, the reaction is carried out in the vapor form. Reaction temperatures may be employed, for example in the range from 125° C. to 300° C., e.g., from 200° C. to 290° C., or from 225° C. to 275° C. Without being bound to one particular theory, different reaction temperatures favor different reaction products. For example, reaction temperatures less than 350° C. may favor the formation of ethanol, whereas temperatures greater than 350° C. may favor the formation of acetaldehyde.

The reaction may be conducted at subatmospheric, atmospheric or superatmospheric pressures. Without being bound to any particular theory, operating the reaction at higher pressures increases the ethanol selectivity of a catalyst comprising molybdenum carbide and a promoter metal. In some embodiments, the pressure may range from 10 KPa to 3000 KPa, e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce a mole of ethanol, the actual molar ratio of acetic acid to hydrogen in the feed stream may be varied between wide limits, e.g. from about 100:1 to 1:100. It is preferred however that such ratio be in the range of about 1:20 to 1:2. More preferably the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 Grady et al., which discloses a process for converting waste biomass through gasification into synthesis gas as well as U.S. Pat. No. 6,685,754 Kindig et al., the disclosures of which are incorporated herein by reference.

In some embodiments, some or all of the raw materials for the above-described acetic acid hydrogenation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 of Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Some embodiments of the process of hydrogenating acetic acid to form ethanol according to one embodiment of the invention may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

Operating under the conditions of the present invention may have an ethanol production on the order of at least 0.1 tons of ethanol per hour, at least 5 tons of ethanol per house, or preferably at least 5 tons of ethanol per hour. Large scale industrial production of ethanol, depending on the scale, generally should be at least 15 tons of ethanol per hour, preferably at least 30 tons of ethanol per hour. In terms of ranges for large scale industrial production of ethanol, the process of the present invention may produce 15 to 160 tons of ethanol per hour, preferably 30 to 80 tons of ethanol per hour. Ethanol production from fermentation, due the economies of scale, typically does not permit large scale ethanol production in one facility that may be achievable by embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will be present in the crude ethanol product, for example, in amounts ranging from 5 to 35 wt. %, e.g., from 10 to 30 wt. % or from 10 to 26 wt. %.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in the crude ethanol product in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
| --- | --- | --- | --- | --- |
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Ethanol may be recovered from the crude ethanol product using one or more distillation columns. The final ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 2.

TABLE 2

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 2, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In one of the preferred embodiments there is also provided a process for selective and direct formation of ethanol from acetic acid comprising: contacting a feed stream containing acetic acid and hydrogen at an elevated temperature with a suitable hydrogenating catalyst containing about 1 weight percent to about 15 weight percent of cobalt on a suitable catalyst support and a second metal supported on said support and wherein said second metal is selected from the group consisting of palladium, platinum, copper, tin, molybdenum and tungsten.

In this embodiment of the process of this invention, the preferred hydrogenation catalyst contains one (1) weight percent palladium or platinum with about ten (10) weight percent cobalt. In this embodiment of the process of this invention it is preferred that the hydrogenation catalysts is layered in a fixed bed and the reaction is carried out in the vapor phase using a feed stream of acetic acid and hydrogen in the molar range of about 1:20 to 1:2 and at a temperature in the range of about 225° C. to 275° C. and at a pressure of reaction zones in the range of about 10 to 25 atmospheres absolute, and the contact time of reactants is in the range of about 0.5 and 100 seconds.

In another embodiment of the process of this invention, the preferred hydrogenation catalyst contains 0.1 to 5 wt. % iron with about 5 to 20 wt. % cobalt. In this embodiment of the process of this invention it is preferred that the hydrogenation catalysts is layered in a fixed bed and the reaction is carried out in the vapor phase using a feed stream of acetic acid and hydrogen in the molar range of about 1:20 to 1:2 and at a temperature in the range of about 225° C. to 275° C. and at a pressure of reaction zones in the range of about 10 KPa to 3000 KPa, and the contact time of reactants is in the range of about 0.5 and 100 seconds.

In order that the invention disclosed herein may be more efficiently understood, the following examples are provided below. It should be understood that these examples are for illustrative purposes only and is not to be construed as limiting the invention in any manner.

EXAMPLES

Example A

Preparation of 10 Weight Percent Cobalt and 1 Weight Percent Palladium on Graphite Powdered and meshed graphite (100 g) of uniform particle size distribution of about 0.2 mm was dried at 120° C. in an oven under nitrogen atmosphere overnight and then cooled to room temperature. To this was added a solution of palladium nitrate (Heraeus) (2.2 g) in distilled water (22 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of cobalt nitrate hexahydrate (49.4 g) in distilled water (50 ml). The resulting slurry was dried in an oven gradually heated to 110° C. (>2 hours, 10° C./min). The impregnated catalyst mixture was then calcined at 500° C. (6 hours, 1° C./min).

Example B

Preparation of 5 Weight Percent Cobalt and 0.5 Weight Percent Palladium on Graphite Powdered and meshed graphite (100 g) of uniform particle size distribution of about 0.2 mm was dried at 120° C. in an oven under nitrogen atmosphere overnight and then cooled to room temperature. To this was added a solution of palladium nitrate (Heraeus) (1.1 g) in distilled water (11 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of cobalt nitrate hexahydrate (24.7 g) in distilled water (25 ml). The resulting slurry was dried in an oven gradually heated to 110° C. (>2 hours, 10° C./min). The impregnated catalyst mixture was then calcined at 500° C. (6 hours, 1° C./min).

Example C

Preparation of 10 Weight Percent Cobalt and 1 Weight Percent Platinum on High Purity Silica Powdered and meshed high purity silica (100 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of cobalt nitrate hexahydrate (49.4 g) in distilled water (50 ml). The resulting slurry was dried in an oven gradually heated to 110° C. (>2 hours, 10° C./min). The impregnated catalyst mixture was then calcined at 500° C. (6 hours, 1° C./min).

Example D

Preparation of 10 Weight Percent Cobalt and 1 Weight Percent Platinum on Calcium Silicate Powdered and meshed calcium silicate (100 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min.). The impregnated catalyst mixture was then calcined at 500° C. (6 hours, 1° C./min.). To this calcined and cooled material was added a solution of cobalt nitrate hexahydrate (49.4 g) in distilled water (50 ml). The resulting slurry was dried in an oven gradually heated to 110° C. (>2 hours, 10° C./min). The impregnated catalyst mixture was then calcined at 500° C. (6 hours, 1° C./min).

Example E

Preparation of 10 Weight Percent Cobalt and 1 Weight Percent Chromium on Graphite Powdered and meshed graphite (100 g) of uniform particle size distribution of about 0.2 mm was dried at 120° C. in an oven under nitrogen atmosphere overnight and then cooled to room temperature. To this was added a solution of chromium nitrate nonahydrate (Alfa Aesar) (6.5 g) in distilled water (13 ml). The resulting slurry was dried in an oven gradually heated to 110° C. (>2 hours, 10° C./min.). The impregnated catalyst mixture was then calcined at 500° C. (6 hours, 1° C./min.). To this calcined and cooled material was added a solution of cobalt nitrate hexahydrate (49.4 g) in distilled water (50 ml). The resulting slurry was dried in an oven gradually heated to 110° C. (>2 hours, 10° C./min.). The impregnated catalyst mixture was then calcined at 500° C. (6 hours, 1° C./min.). Gas Chromatographic (GC) analysis of the Products Example F Preparation of 5 Weight Percent Iron and 5 Weight Percent Cobalt on High Purity, Low Surface Area Silica Powdered and meshed high purity, low surface area silica (90 g) of uniform particle size distribution of about 0.2 mm was dried at 120° C. in an oven under nitrogen atmosphere overnight and then cooled to room temperature. To this was added a solution of iron nitrate nonahydrate (Alfa Aesar) (36.2 g) in distilled water (30 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of cobalt nitrate hexahydrate (24.7 g) in distilled water (25 ml). The resulting slurry was dried in an oven gradually heated to 110° C. (>2 hours, 10° C./min). The impregnated catalyst mixture was then calcined at 500° C. (6 hours, 1° C./min).

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene Diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

Example 1

The catalyst utilized was 10 weight percent cobalt and 1 weight percent palladium on Graphite prepared in accordance with the procedure of Example A In a tubular reactor made of stainless steel, having an internal diameter of 30 mm and capable of being raised to a controlled temperature, there are arranged 50 ml of 10 weight percent cobalt and 1 weight percent palladium on Graphite. The length of the catalyst bed after charging was approximately about 70 mm A feed liquid was comprised essentially of acetic acid. The reaction feed liquid was evaporated and charged to the reactor along with hydrogen and helium as a carrier gas with an average combined gas hourly space velocity (GHSV) of about 2500 $hr^{-1}$ at a temperature of about 250° C. and pressure of 22 bar. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to ethanol was 97.5% at a conversion of acetic acid of 18.5%.

Example 2

The catalyst utilized was 5 weight percent cobalt and 0.5 weight percent platinum on graphite prepared in accordance with the procedure of Example B.

The procedure as set forth in Example 1 is substantially repeated with an average combined gas hourly space velocity (GHSV) of 2,500 $hr^{-1}$ of the feed stream of the vaporized acetic acid and hydrogen at a temperature of 225° C. and pressure of 22 bar. A portion of the vapor effluent is passed through a gas chromatograph for analysis of the contents of the effluents. The acetic acid conversion is 20% and ethanol selectivity is 95%.

Example 3

The catalyst utilized was 10 weight percent cobalt and 1 weight percent platinum on High Purity Silica prepared in accordance with the procedure of Example C.

The procedure as set forth in Example 1 was substantially repeated with an average combined gas hourly space velocity (GHSV) of 2,500 $hr^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion was 71% and ethanol selectivity was 96%.

Example 4

The catalyst utilized was 10 weight percent cobalt and 1 weight percent platinum on calcium silicate prepared in accordance with the procedure of Example D.

The procedure as set forth in Example 1 was substantially repeated with an average combined gas hourly space velocity (GHSV) of 2,500 $hr^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion was 50% and ethanol selectivity was 94%.

Example 5

The catalyst utilized was 10 weight percent cobalt and 1 weight percent chromium on graphite prepared in accordance with the procedure of Example E.

The procedure as set forth in Example 1 is substantially repeated with an average combined gas hourly space velocity (GHSV) of 2,500 $hr^{-1}$ of the feed stream of the vaporized acetic acid and hydrogen at a temperature of 250° C. and pressure of 22 bar. A portion of the vapor effluent was passed through a gas chromatograph for analysis of the contents of the effluents. The acetic acid conversion is 38% and ethanol selectivity is 96%.

Example 6

In a tubular reactor made of stainless steel, having an internal diameter of 30 mm and capable of being raised to a controlled temperature, a catalyst was arranged comprising 17.4 wt. % cobalt and 4.8 wt. % iron on silica. The length of the catalyst bed after charging was approximately 70 mm.

A feed liquid of acetic acid was evaporated and charged to the reactor along with hydrogen and helium as a carrier gas with an average combined gas hourly space velocity (GHSV) of about 2500 $hr^{-1}$ at a temperature of about 225° C. and pressure of 14 barg. The cobalt and iron catalyst demonstrated a selectivity to ethanol of 76.8%. The selectivity of ethoxylates was 98.1%. The selectivity to ethane was 1.9%.

Example 7

The reactor and procedure of Example 6 was repeated with the reaction conditions set forth below.

A feed liquid of acetic acid was evaporated and charged to the reactor along with hydrogen and helium as a carrier gas with an average combined gas hourly space velocity (GHSV) of about 2500 $hr^{-1}$ at a temperature of about 250° C. and pressure of 14 barg. The cobalt and iron catalyst demonstrated a selectivity to ethanol of 73.6% with a conversion of acetic acid of 40.7%. The selectivity of ethoxylates was 95.2%. The selectivity to ethane was 1.8%.

Example 8

Comparative

The catalyst utilized was a commercially available Co/Fe catalyst containing 17.4 weight percent cobalt and 4.8 weight percent iron on silica.

In a tubular reactor made of stainless steel, having an internal diameter of 30 mm and capable of being raised to a controlled temperature, there are arranged 50 ml of 1 weight percent ruthenium supported on iron oxide. The length of the catalyst bed after charging was approximately about 70 mm. Prior to the reaction the catalyst was reduced in situ by heating at a rate of 2° C./min to a final temperature of 400° C. Then, 5 mol % hydrogen in nitrogen was introduced to the catalyst chamber at a gas hourly space velocity (GHSV) of 7500 $h^{-1}$. After reduction, the catalyst was cooled to reaction temperature of 350° C. by continuing the gas flow of 5 mol % hydrogen in nitrogen. Once the reaction temperature was stabilized at 350° C., the hydrogenation of acetic acid was begun as follows.

A feed liquid was comprised essentially of acetic acid. The reaction feed liquid was evaporated and charged to the reactor along with hydrogen and helium as a carrier gas with an average combined gas hourly space velocity (GHSV) of about 2500 $hr^{-1}$ at a temperature of about 350° C. A portion of the vapor effluent is passed through a gas chromatograph for analysis of the contents of the effluents. The acetic acid conversion is about 65% and acetaldehyde selectivity is 75%.

The higher reaction temperature of comparative Example 8 is believed to contribute to increased selectivity to acetaldehyde over ethanol. When operating at lower temperature, such as shown in Example 6, the selectivity to ethanol is favored.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

We claim:

1. A process for selective and direct formation of ethanol from acetic acid comprising: contacting a feed stream comprising acetic acid and hydrogen in vapor form at a temperature of 125° C. to 300° C. with a hydrogenation catalyst comprising cobalt and one or more metals selected from the group consisting of palladium, platinum, rhodium, ruthenium, rhenium, iridium, chromium, copper, tin, molybdenum, tungsten, vanadium, zinc, and iron on a catalyst support.

2. The process of claim 1, wherein the catalyst is selected from the group consisting of zeolite, iron oxide, silica, alumina, titania, zirconia, silica-alumina, magnesium oxide, calcium silicate, carbon, graphite and mixtures thereof.

3. The process of claim 1, wherein the catalyst support is selected from the group consisting of silica, silica/alumina, calcium metasilicate, pyrogenic silica, high purity silica and mixtures thereof.

4. The process of claim 1, wherein the loading of cobalt is from 0.1 wt. % to 20 wt. %.

5. The process of claim 1, wherein the loading of the one or more metals is from 0.1 wt. % to 20 wt. %.

6. The process of claim 1, wherein the one or more metals comprises iron.

7. The process of claim 6, wherein the loading of cobalt is from 0.1 to 20 wt. % and the loading of iron is from 0.1 to 10 wt. %.

8. The process of claim 1, wherein the process yields an acetic acid conversion of at least 10%.

9. The process of claim 1, wherein the hydrogenation catalyst has a selectivity to ethanol of at least 40%.

10. The process of claim 1, wherein the hydrogenation catalyst has a selectivity to methane, ethane, and carbon dioxide of less than 4%.

11. The process of claim 1, wherein the hydrogenation catalyst has a selectivity to ethoxylates of at least 40%.

12. The process of claim 1, wherein the hydrogenation of acetic acid is carried out at a pressure of 10 KPa to 3000 KPa.

13. The process of claim 1, wherein the hydrogenation catalyst further comprises a support modifier.

14. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

15. A process for selective and direct formation of ethanol from acetic acid comprising: contacting a feed stream comprising acetic acid and hydrogen in vapor form at a temperature of 125° C. to 300° C. with a hydrogenation catalyst comprising from 0.1 wt. % to 20 wt. % cobalt and from 0.1 wt. % to 20 wt. % iron on a catalyst support.

16. The process of claim 15, wherein the loading of cobalt is from 5 to 20 wt. % and the loading of iron is from 0.1 to 10 wt. %.

17. The process of claim 15, wherein the catalyst is selected from the group consisting of zeolite, iron oxide, silica, alumina, titania, zirconia, silica-alumina, magnesium oxide, calcium silicate, carbon, graphite and mixtures thereof.

18. The process of claim 15, wherein the catalyst support is selected from the group consisting of silica, silica/alumina, calcium metasilicate, pyrogenic silica, high purity silica and mixtures thereof.

19. The process of claim 15, wherein the process yields an acetic acid conversion of at least 10%.

20. The process of claim 15, wherein the hydrogenation catalyst has a selectivity to ethanol of at least 40%.

* * * * *